(12) United States Patent
Rozema et al.

(10) Patent No.: US 7,871,818 B2
(45) Date of Patent: Jan. 18, 2011

(54) MEMBRANE ACTIVE POLYMERS

(75) Inventors: David B. Rozema, Madison, WI (US); Darren Wakefield, Fitchburg, WI (US)

(73) Assignee: Roche Madison Inc., Madison, WI (US)

( * ) Notice: Subject to any disclaimer, the term of this patent is extended or adjusted under 35 U.S.C. 154(b) by 0 days.

(21) Appl. No.: 10/765,668

(22) Filed: Jan. 27, 2004

(65) Prior Publication Data

US 2004/0151775 A1 Aug. 5, 2004

Related U.S. Application Data

(60) Provisional application No. 60/443,906, filed on Jan. 31, 2003.

(51) Int. Cl.
*C12N 15/00* (2006.01)
*C12N 15/09* (2006.01)
*A61K 9/14* (2006.01)

(52) U.S. Cl. .................. 435/455; 435/440; 424/486

(58) Field of Classification Search ............. 514/772.2, 514/784, 785, 788
See application file for complete search history.

(56) References Cited

U.S. PATENT DOCUMENTS

| 4,732,933 | A  | * | 3/1988  | Maeda et al. ............. 424/78.21 |
| 5,118,551 | A  | * | 6/1992  | Calcaterra et al. ............. 428/96 |
| 6,211,250 | B1 | * | 4/2001  | Tomlinson et al. ....... 514/772.4 |
| 6,436,905 | B1 | * | 8/2002  | Tonge et al. ................... 514/23 |
| 6,740,336 | B2 | * | 5/2004  | Trubetskoy et al. ......... 424/450 |
| 6,835,393 | B2 | * | 12/2004 | Hoffman et al. ............. 424/450 |
| 2002/0052335 | A1 | * | 5/2002 | Rozema et al. ................ 514/44 |
| 2005/0153926 | A1 | * | 7/2005 | Adams et al. ................. 514/44 |

FOREIGN PATENT DOCUMENTS

| GB | 1241294       | * | 8/1971 |
| WO | WO 0149841 A1 | * | 7/2001 |

OTHER PUBLICATIONS

Maeda et al. Mechanism of tumor-targeted delivery of macromolecular drugs, including the EPR effect in solid tumor and clinical overview of the prototype polymeric drug SMANCS. J Control Release. vol. 74, No. 1-3, pp. 47-61, Jul. 2001.*
Saettone et al. Inserts for sustained ocular delivery of pilocarpine: Evaluation of a series of partial esters of (maleic acid- alkyl vinyl ether) alternating copolymers. Polymers in Medicine III, vol. 5, pp. 209-224, 1988.*
Verma et al. Gene therapy—promises, problems and prospects. Nature. vol. 389, No. 6648, pp. 239-242, Sep. 1997.*
Palu et al. In pursuit of new developments for gene therapy of human diseases. J Biotechnol. vol. 68, No. 1, pp. 1-13, Feb. 1999.*
Luo et al. Synthetic DNA delivery systems. Nat Biotechnol. vol. 18, No. 1, pp. 33-37, Jan. 2000.*
Edelstein et al. Gene therapy clinical trials worldwide 1989-2004—an overview. J Gene Med. vol. 6, No. 6, pp. 597-602, Jun. 2004.*
Yu et al. Topical Gene Delivery to Murine Skin. The Journal of Investigative Dermatology, vol. 112, No. 3, pp. 370-375, 1999.*
Salamone, J.C. "Maleimide Copolymers (N-Substituted)" in Polymeric Materials Encyclopedia. CRC Press, pp. 3996-4013, 1996.*
Heller et al. Controlled drug release by polymer dissolution. I. Partial esters of maleic anhydride copolymers—Paroperties and Theory. Journal of Applied Polymer Science, vol. 22, pp. 1991-2009, 1978.*
Saettone et al. "Inserts for Sustained Ocular Delivery of Pilocarpine: Evaluation of a Series of Partial Esters of (Maleic Acid—Alkyl Vinyl Ether) Alternating Copolymers." Polymers in Medicine III: Third International Conference on Polymers in Medicine. Ed. Migliarese, C., et al. Elsevier Science Publishers B.V., pp. 209-224, 1998.*
Akhtar S et al. "Interactions of antisense DNA oligonucleotide analogs with phospholipid membranes liposomes." Nucleic Acids Res; 1991 vol. 19 No. 20 pp. 5551-5559.
Akhtar S et al. "The delivery of antisense therapeutics." Adv Drug Deliv Rev; 2000 vol. 44 No. 1 pp. 3-21.
Audouy S et al. "Cationic lipid-mediated transfection in vitro and in vivo." Mol Membr Biol; 2001 vol. 18 No. 2 pp. 129-143.
Berg T et al. "Physiological functions of endosomal proteolysis." Biochem J; 1995 vol. 307 No. 2 pp. 313-326.
Borszeky K et al. "Enantioselective hydrogenation of [α],[β]-unsaturated acids. Substrate-modifier interaction over cinchonidine modified Pd/Al2O3." Tetrahedron Asymmetry; 1997 vol. 8 No. 22 pp. 3745-3753.
Carrasco L "Entry of animal viruses and macromolecules into cells." FEBS Lett; 1994 vol. 350 No. 2-3 pp. 151-154.
Cheung CY et al. "A pH-sensitive polymer that enhances cationic lipid-mediated gene transfer." Bioconjug Chem; 2001 vol. 12 No. 6 pp. 906-910.
Danko I et al. "High expression of naked plasmid DNA in muscles of young rodents." Hum Mol Genet; 1997 vol. 6 No. 9 pp. 1435-1443.
Ghosh C et al. "Intracellular delivery strategies for antisense phosphorodiamidate morpholino oligomers." Antisense Nucleic Acid Drug Dev; 2000 vol. 10 No. 4 pp. 263-274.
Giles RV et al. "Antisense morpholino oligonucleotide analog induces missplicing of C-myc mRNA." Antisense Nucleic Acid Drug Dev; 1999 vol. 9 No. 2 pp. 213-220.
Heasman J et al. "Beta-catenin signaling activity dissected in the early Xenopus embryo: a novel antisense approach." Dev Biol; 2000 vol. 222 No. 1 pp. 124-134.
Hope MJ et al. "Cationic lipids, phosphatidylethanolamine and the intracellular delivery of polymeric, nucleic acid-based drugs." Mol Membr Biol; 1998 vol. 15 No. 1 pp. 1-14.
Kang SH et al. "Up-regulation of luciferase gene expression with antisense oligonucleotides: implications and applications in functional assay development." Biochemistry; 1998 vol. 37 No. 18 pp. 6235-6239.
Kyriakides TR et al. "pH-sensitive polymers that enhance intracellular drug delivery in vivo." J Control Release; 2002 vol. 78 No. 1-3 pp. 295-303.
Lackey CA et al. "Hemolytic Activity of pH-Responsive Polymer-Streptavidin Bioconjugates." Bioconjugate Chem; 1999 vol. 10 No. 3 pp. 401.

(Continued)

*Primary Examiner*—Jennifer Dunston
(74) *Attorney, Agent, or Firm*—Kirk Ekena

(57) ABSTRACT

We describe a class of polymaleic anhydride polymers capable of disrupting cell membranes. Co-delivery of these polymers with biologically active compounds increases cellular cytoplasmic delivery of the compounds.

4 Claims, 3 Drawing Sheets

OTHER PUBLICATIONS

Lackey et al. "A biomimetic pH-responsive polymer directs endosomal release and intracellular delivery of an endocytosed antibody complex." Bioconjug Chem. 2002 vol. 13 No. 5 pp. 996-1001.

Lai MZ et al. "Effects of replacement of the hydroxyl group of cholesterol and tocopherol on the thermotropic behavior of phospholipid membranes." Biochemistry; 1985 vol. 24 No. 7 pp. 1646-1653.

Lai MZ et al. "Acid- and calcium-induced structural changes in phosphatidylethanolamine membrane stabilized by cholesteryl hemisuccinate." Biochem 1985 vol. 25 pp. 1654-1661.

Maeda H et al. "Mechanism of tumor-targeted delivery of macromolecular drugs, including the EPR effect in solid tumor and clinical overview of the prototype polymeric drug SMANCS." J Control Release; 2001 vol. 74 pp. 47-61.

Mukherjee S et al. "Endocytosis." Physiol Rev; 1997 vol. 77 No. 3 pp. 759-803.

Murthy N et al. "The design and synthesis of polymers for eukaryotic membrane disruption." J Control Release 1999 vol. 61 pp. 137-143.

Nasevicius A et al. "Effective targeted gene 'knockdown' in zebrafish." Nat Genet; 2000 vol. 26 No. 2 pp. 216-220.

Oda T et al. "Facilitated internalization of neocarzinostatin and its lipophilic polymer conjugate, SMANCS, into cytosol in acidic pH." J Natl Cancer Inst; 1987 vol. 79 No. 6 pp. 1205-1211.

Plank C et al. "Application of membrane-active peptides for drug and gene delivery across cellular membranes." Adv Drug Deliv Rev 1998 vol. 34 No. 1 pp. 21-35.

Plank C. et al. "The influence of endosome-disruptive peptides on gene transfer using synthetic virus-like gene transfer systems." J Biol Chem 1994 vol. 269 No. 17 pp. 12918-12924.

Robaczewska MS et al. "Inhibition of hepadnaviral replication by polyethylenimine-based intravenous delivery of antisense phosphodiester oligodeoxynucleotides to the liver." Gene Ther; 2001 vol. 8 No. 11 pp. 874-881.

Skehel JJ et al. "Receptor binding and membrane fusion in virus entry: the influenza hemagglutinin." Annu Rev Biochem; 2000 vol. 69 pp. 531-569.

Summerton J et al. "Morpholino antisense oligomers: design, preparation, and properties." Antisense Nucleic Acid Drug Dev; 1997 vol. 7 No. 3 pp. 187-195.

Wolff JA et al. "Direct gene transfer into mouse muscle in vivo." Science 1990 vol. 247 pp. 1465-1468.

Zuber G et al. "Towards synthetic viruses." Adv Drug Deliv Rev; 2001 vol. 52 No. 3 pp. 245-253.

Yessine M-A. "Membrane-destabilizing polyanions: interaction with lipid bilayers and endosomal escape of biomacromolecules." Advanced Drug Delivery Reviews 2004 vol. 56, p. 999-1021.

Tsiourvas D et al. "Further studies on Homopolymers and Copolymers Resulting from the Reaction of Polymaleic anhydride with alcohols and amines." J Polymer Science 1990 vol. 28 pp. 1263-1271.

* cited by examiner

MEMBRANE ACTIVE POLYMERS

CROSS-REFERENCE TO RELATED APPLICATIONS

This application is related to prior U.S. Provisional Application Ser. No. 60-443906 filed 31 Jan. 2003.

BACKGROUND OF THE INVENTION

The route of cellular entry for most conventional drugs is diffusion across the biological membrane. For this reason, drugs tend to be small (MW<500) and amphipathic, containing both hydrophobic and hydrophilic functionalities. These characteristics engender molecules with water solubility, while allowing them to cross the nonpolar lipid bilayer of the cell membrane. In contrast, the drugs used in antisense and gene therapies are relatively large hydrophilic polymers and frequently highly negatively charged nucleic acids as well. Both of these physical characteristics preclude their direct diffusion across the cell membrane. For this reason, the major barrier to gene therapy and antisense therapy is the delivery of the drug to the cellular interior. This situation is in contrast to standard drug development in which the identification of the drug is the major barrier in development.

The route of entry for most macromolecules such as DNA and oligonucleotides into cells is endocytosis. Once taken into the cell, the endosome is either recycled back to the cell surface, or matures to a late endosome and finally to a lysosome. In this process, the pH gradually drops from 7 to 6 as the early endosome becomes a late endosome. In the late endosome, the pH drops from 6 to less than 5 as it matures into a lysosome. In the late endosome and lysosome, enzymes such as proteases, nucleases, and glycosylases digest hydrolyzable components in the compartment. To prevent degradation of nucleic acids and other potential drugs in the lysosome, the endosome must be disrupted, and the contents released, prior to its evolution into a lysosome. Once endocytosis occurs, the endosome becomes a late endosome within about 10 minutes [Mukherjee et al. 1997]. The late endosome contains hydrolytic enzymes such as proteases [Berg et al. 1995] and other hydrolytic enzymes. Additional digestive enzymes become present as the endosome evolves into a lysosome.

For material to escape from endosomes into the cytoplasm, the membrane of the endosome must be disrupted. Endosome rupture can occur by osmotic pressure causing the membrane to swell and burst [Zuber et al. 2001], by membrane disruptive agents that denature the membrane bilayer structure, or a combination of these forces. Methods for accomplishing endosomal release often rely upon the environment of the lysosome and/or endosome to trigger membrane rupture and release of its contents. For example, vectors may be substrates for lysosomal enzymes such as proteases. Proteolysis can result a activation of a membrane active compound which then destabilizes the bilayer. An example of enzyme-triggered membrane breakage is adenoviral coat proteins which change structure and membrane disruptive ability upon proteolytic cleavage [Skehel et al 2000].

The drop in pH as an endosome matures into a lysosome may also be utilized to trigger membrane disruption and content release. Viral infections often require the acidification of the endosomal compartment [Carrascol994]. To mimic this viral activity synthetically, many nonviral transfections agents have been designed with pH-dependent components. Agents that are weakly basic, $pK_a$ 5-7, can be reversibly protonated in the acidic environment of the endosome. Examples include chloroquine, polyethyleneimine, and histidylated poly-L-lysine. The effect of these buffering compounds is to increase the number of protons required for a drop in pH. It is postulated that the increased number of protons, and as a consequence their counterions, causes an increase in the osmotic pressure of the endosome, which leads to membrane rupture, the proton sponge effect [Zuber et al. 2001].

Another mechanism for pH-dependent membrane disruption is the use of agents whose interaction with a membrane is dependent upon its protonation, e.g. cholesterol hemisuccinate [Lai et al. 1985], viral coat peptides and their derivatives [Plank et al. 1998], and polypropylacrylic acid (PPA) [Cheung et al. 2001]. A common characteristic of these agents is that they are carboxylic acid- and hydrophobic group-containing molecules that become less charged as the pH drops. The decrease in charge renders the molecules more hydrophobic, and thus more membrane disruptive.

The most studied synthetic carboxylate-containing polymer for endosome disruption is PPA [Lackey et al. 2002]. The propyl group in each monomer of PPA constitute the hydrophobic groups of the polymer. Another synthetic carboxylate-containing polymer is polyethylacrylic acid (PEA). PEA is also membrane-active in a pH-dependent manner. However, depending on the molecular weight of the polymer, the onset of membrane activity for PEA occurs well below pH 6. By increasing the length of the hydrophobic group of PEA by one carbon, to produce PPA, the pH-dependence of the polymer shifts to less acidic conditions such that the onset of membrane activity occurs the more physiologically relevent pH 6.5. In addition to polyacrylic acids, polyamino acid polymers containing aspartate or glutamate residues also exhibit pH sensitive charge negative charge. Many naturally-occurring pH-sensitive polymers rely on these anionic residues for their pH dependence.

SUMMARY OF THE INVENTION

In a preferred embodiment, we describe a class of maleic anhydride-based anionic polymers capable of disrupting cell membranes. The polymers may by homopolymers, random copolymers or alternating copolymers. Hydrophobic groups are incorporated into the polymers through copolymerization with hydrophobic monomers or by reacting hydrophobic groups with anhydrides in the polymer.

In a preferred embodiment the described polymers can be used to deliver biologically active compounds to cells in vivo or in vitro. The polymers facilitate release of biologically active compounds from vesicles into the cytoplasm following co-endocytosis of the polymer and the compound. In one embodiment, the biologically active compound and the polymer are associated with the cell such that both molecules are endocytosed by the cell. In another embodiment the biologically active compound and the polymer are associated to each other via non-covalent interaction to form a complex. The complex is then associated with the cell. In another embodiment, the biologically active compound is covalently linked to the polymer. The polymer-compound molecule is then associated with the cell.

In a preferred embodiment, the functionality of the polymer may be modified or enhanced by covalent attachment of functional groups. Functional groups may be added to the polymer though copolymerization or through reaction with an anhydride in the polymer.

Further objects, features, and advantages of the invention will be apparent from the following detailed description when taken in conjunction with the accompanying drawings.

DETAILED DESCRIPTION

Figure 1:
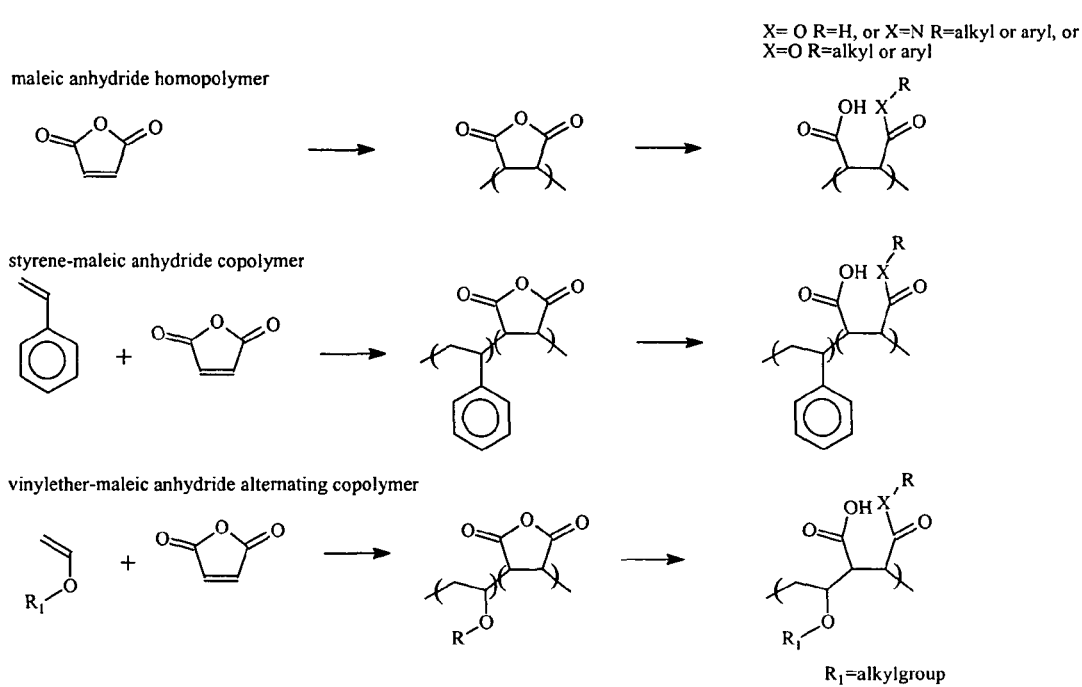
FIG. 1 Illustration of formation of polyanions based on polymerization of maleic anhydride: homopolymers, random copolymers, and alternating copolymers. Carboxyl groups are shown in protonated form.

We describe a new class of anionic polymers that can be used to deliver biologically active compounds to cells. These polymers contain maleic anhydride monomers and facilitate release of biologically active compounds from vesicles after endocytosis. Synthetic polyanions based on polymerization of maleic anhydride are shown in FIG. 1. Maleic anhydride polymerized by radical initiation may polymerize with itself to form a homopolymer to form maleic anhydride homopolymers, or may polymerize with comonomers such as styrene or vinyl ethers to form maleic anhydride copolymers. Styrene itself polymerizes by radical-based mechanism; therefore, copolymers of styrene and maleic anhydride (styrene-maleic anhydride-based copolymers) are random, i.e. the total composition of the polymer is dependent upon the ratio of the monomers, but that the order of the monomers is random. In contrast, vinyl ether monomers do not polymerize by radical polymerization unless reacting with maleic anhydride; therefore, polymers composed of maleic anhydride and vinyl ethers (vinyl ether-maleic anhydride-based copolymers) are alternating, i.e. vinyl ether monomer is followed by maleic anhydride monomer followed by vinyl ether and so on. The resulting polymers contain anhydride groups. These anhydride groups may then be hydrolyzed to form diacid groups. Alternatively, the polymers may be reacted with alcohols and/or amines to form acids and esters and/or amides. The resulting polymers contains 1-2 carboxylate groups for each maleic anhydride. The polymers are therefore polyanions.

Figure 2:
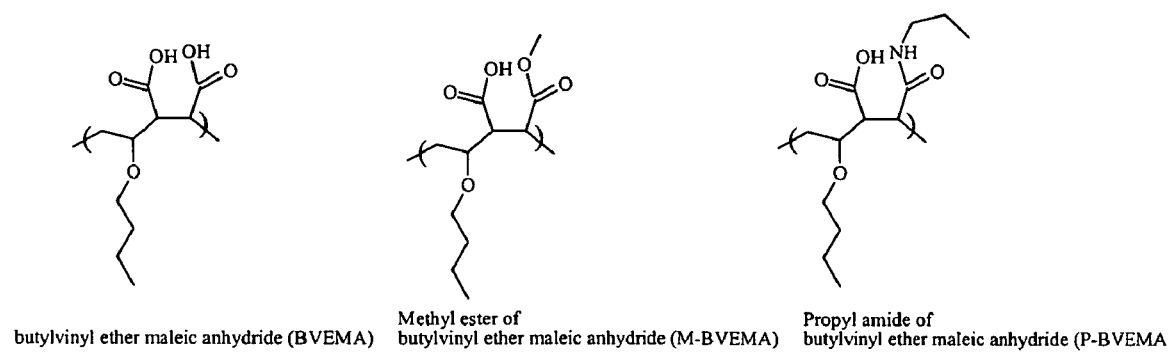
FIG. 2 Illustration of polymers synthesized by polymerization of butyl vinyl ether maleic anhydride polymer (BVEMA) with alcohols and amines to form esters and amides. Carboxyl groups are shown in protonated form.

Hydrophobic groups may be incorporated into maleic anhydride-derived polyanions by copolymerization with styrene or vinyl ether (FIG. 1 & 2), and/or reacting the polyanhydride with any molecule (including, but not limited to, alcohols and amines) capable of reacting with an anhydride to form a covalent linkage such that at least one carboxyl remains on the anhydride monomer. Those skilled in the art will readily recognize that the molecule can form a covalent linkage with either carbonyl of the anhydride (FIG. 2). Reaction of hydrophobic alcohols and/or hydrophobic amines with anhydride moieties in the polyanhydride results in the formation of hydrophobic esters and/or hydrophobic amides of polymaleic acid. The resulting polyanions can acquire hydrophobicity from alkyl groups on the vinyl ether, the phenyl group of styrene or from molecules reacted with the anhydride. Vinyl ethers may be selected from the group consisting of: alkyl vinyl ether, aryl vinyl ethers and the like.

Other molecules capable of reacting with an anhydride may also be covalently linked to the polymer. Molecules that may be attached to the polymer may be selected from the list comprising: biologically active compounds, cell targeting signals, interaction modifiers, steric stabilizers, reporter molecules, and other groups designed to add function to the polymer or increase utility of the polymer.

The copolymer of styrene and maleic anhydride (SMA) has been studied as a drug delivery agent [Maeda et al. 2001]. Various derivatives of SMA have been synthesized in which various alkyl groups have been incorporated into the polymer by reaction with the anhydride. Specifically, a drug delivery polymer has been synthesized by reaction of the anhydrides of SMA with butyl alcohol-to produce a polymer containing both butyl and phenyl groups—followed by conjugation to the anticancer drug neocarzinostatin (NC). The resulting drug-conjugated polymer, SMANC, has been approved for cancer treatments in Japan. SMANC and other macromolecular drug-conjugated polyanions have been used to target drugs to tumors through a phenomenon of solid tumors termed enhanced permeability and retention (EPR). The EPR effect is a function of the hypervasculaturization and defective vascular architecture associated with solid tumors. This unusual vasculature results in increased permeability of the tumor vessels and retention of large molecules. The EPR effect facilitates extravasation of polymeric drugs more selectively at tumor tissues and is a widely invoked mechanism for the targeting of a variety of polymers to tumors.

Described are maleic anhydride-containing polymers for delivery of biologically active compounds to the cytoplasm of cells via endocytosis, not merely as vehicles for EPR-based delivery of drugs to the cell surface. These polymers are capable of disrupting intracellular membranes following endocytosis. We have investigated alternating copolymers of various alkyl vinyl ethers and maleic anhdyride. The anhydride groups of these polymers may be hydrolyzed to form diacids or reacted with other molecules, such as alcohols and/or amines to produce esters and/or amides. These polymers are easily synthesized from the commercially available monomers: alkyl vinyl ethers and maleic anhydride. In contrast the polymer PPA is synthesized from a monomer that is the product of a 4-step synthesis [Borszeky et al. 1997]. The resulting maleic anhydride-vinyl ether copolymers contain anhydride groups that can be reacted with any nucleophile to easily produce a variety of new polymers.

The maleic anhydride-containing polymers may be screened for their potential for endosomolysis by assaying red blood cell lysis as a function of pH. For example, ethyl, propyl, and butyl vinyl ether were polymerized with maleic anhydride and hydrolyzed to form the diacid monomers. The resultant polyanions were tested for pH-dependent lysis. The butyl vinyl ether based polymer was the only one capable of red blood cell membrane lysis. In contrast, acrylic acid polymers which contain propyl groups are effective at lysis.

Figure 3:
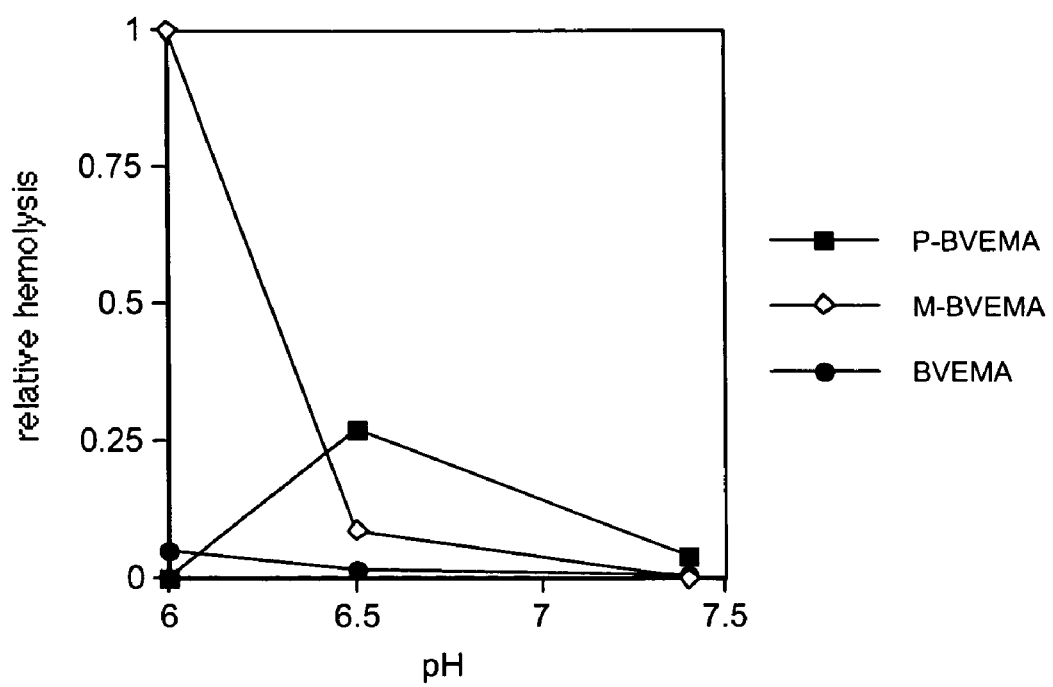
FIG. 3. Graphical illustration of hemolytic potential of BVEMA, M-BVEMA and P-BVEMA polymers.

Polymers formed by reacting the butyl vinyl ether maleic anhydride polymer (BVEMA) with alcohols and amines to form esters and amides are also described (FIG. 2). The methyl ester of BVEMA (M-BVEMA) and the propyl amide of BVEMA (P-BVEMA) were synthesized and tested for their hemolytic activity. The incorporation of both alkyl groups increased the lytic activity of these polymers and the pH at which lytic activity occurs, from pH 6 to 6.5 (FIG. 3). These effects on the membrane activity may be due to the decrease in charge density of the polymer by the formation of ester and amide groups and/or by the increase of hydrophobicity of the polymers.

Delivery of the biologically active compounds to the cell cytoplasm is facilitated by co-endocytosis of the biologically active compounds with the maleic anhydride-containing polymers. In one aspect of the invention, the biologically active compound and the maleic anhydride-containing polymers are not associated with each other but are both endocytosed by the cell. In another aspect of the invention, the biologically active compound and the maleic anhydride-containing polymer are associated with each other via covalent or non-covalent interactions. Non-covalent interactions include ionic interactions, hydrophobic interactions, Van der Waals interactions, and affinity interactions. This association can enable or enhance co-endocytosis of the biologically active compound and the maleic anhydride-containing polymers. The cell can be in vitro or in vivo. For delivery of a biologically active compound to a cell in vivo, the polymer and biologically active compound are inserted into the animal is a manner that permits the polymer and the biologically active compound to come into contact with the cell. Parenteral routes of administration include intravascular, intramuscular, intraparenchymal, intradermal, subdermal, subcutaneous, intratumor, intraperitoneal, intrathecal, subdural, epidural, and intralymphatic injections that use a syringe and a needle or catheter. Other routes of administration include intraparenchymal into tissues such as muscle (intramuscular), liver, brain, and kidney. Epithelial routes include oral, nasal, respiratory, and vaginal routes of administration.

Definitions

To facilitate an understanding of the present invention, a number of terms and phrases are defined below:

A polymer is a molecule built up by repetitive bonding together of smaller units called monomers. The polymer can be linear, branched network, star, comb, or ladder types of polymer. The polymer can be a homopolymer in which a single monomer is used or can be copolymer in which two or more monomers are used.

The main chain of a polymer is composed of the atoms whose bonds are required for propagation of polymer length. For example in poly-L-lysine, the carbonyl carbon, α-carbon, and α-amine groups are required for the length of the polymer and are therefore main chain atoms. The side chain of a polymer is composed of the atoms whose bonds are not required for propagation of polymer length. For example in poly-L-lysine, the β, γ, δ and ε-carbons, and ε-nitrogen are not required for the propagation of the polymer and are therefore side chain atoms.

Other Components of the Monomers and Polymers: Polymers may have functional groups that enhance their utility. These groups can be incorporated into monomers prior to polymer formation or attached to the polymer after its formation. Functional groups may be selected from the list consisting of: targeting groups, interaction modifiers, steric stabilizers, and membrane active compounds, affinity groups and reactive groups.

Targeting groups, or ligands, are used for targeting the polymer or polymer complex to cells, to specific cells, to tissues or to specific locations in a cell. Targeting groups enhance the association of molecules with a cell. Examples of targeting groups include those that target to the asialoglycoprotein receptor by using asialoglycoproteins or galactose residues. Other proteins such as insulin, EGF, or transferrin can be used for targeting. Other targeting groups include molecules that interact with membranes such as fatty acids, cholesterol, dansyl compounds, and amphotericin derivatives. A variety of ligands have been used to target drugs and genes to cells and to specific cellular receptors. The ligand may seek a target within the cell membrane, on the cell membrane or near a cell. Binding of a ligand to a receptor may initiate endocytosis.

A steric stabilizer is a long chain hydrophilic group that prevents aggregation of final polymer by sterically hindering particle to particle electrostatic interactions. Examples include: alkyl groups, PEG chains, polysaccharides, hydrogen molecules, alkyl amines.

An interaction modifier changes the way that a molecule interacts with itself or other molecules, relative to molecule containing no interaction modifier. The result of this modification is that self-interactions or interactions with other molecules are either increased or decreased. For example, polyethylene glycol is an interaction modifier that decreases interactions between molecules and themselves and with other molecules.

Membrane active polymers or compounds are molecules that are able to alter membrane structure. This change in structure can be shown by the compound inducing one or more of the following effects upon a membrane: an alteration that allows small molecule permeability, pore formation in the membrane, a fusion and/or fission of membranes, an alteration that allows large molecule permeability, or a dissolving of the membrane. This alteration can be functionally defined by the compound's activity in at least one the following assays: red blood cell lysis (hemolysis), liposome leakage, liposome fusion, cell fusion, cell lysis and endosomal release. More specifically membrane active compounds allow for the transport of molecules with molecular weight greater than 50 atomic mass units to cross a membrane. This transport may be accomplished by either the total loss of membrane structure, the formation of holes (or pores) in the membrane structure, or the assisted transport of compound through the membrane.

A biologically active compound is a compound having the potential to react with biological components and are designed to change a natural processes associated with a cell. For purposes of this specification, a cellular natural process is a process that is associated with the cell before delivery of the biologically active compound. Biologically active compounds may be selected from the list comprising: pharmaceuticals/drugs, proteins, peptides, enzyme inhibitors, hormones, cytokines, antigens, antibodies, and polynucleotides.

The general structure for a vinyl ether is:

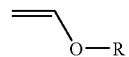

R may be any carbon-containing group. Either of the two carbon atoms may be bonded to hydrogen or carbon atoms.

The general structure for a styrene is:

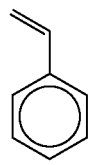

Substitutions may be made at any of the phenyl carbon atoms. Either of the two carbon atoms sharing a double bond may be bonded to hydrogen or carbon atoms.

The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA. The term polynucleotide includes deoxyribonucleic acid (DNA) and ribonucleic acid (RNA) and combinations of DNA, RNA and other natural and synthetic nucleotides.

A polynucleotide can be delivered to a cell to express an exogenous nucleotide sequence, to inhibit, eliminate, augment, or alter expression of an endogenous nucleotide sequence, or to affect a specific physiological characteristic not naturally associated with the cell.

A polynucleotide-based gene expression inhibitor comprises any polynucleotide containing a sequence whose presence or expression in a cell causes the degradation of or inhibits the function, transcription, or translation of a gene in a sequence-specific manner. Polynucleotide-based expression inhibitors may be selected from the group comprising: siRNA, microRNA, interfering RNA or RNAi, dsRNA, ribozymes, antisense polynucleotides, and DNA expression cassettes encoding siRNA, microRNA, dsRNA, ribozymes or antisense nucleic acids. SiRNA comprises a double stranded structure typically containing 15-50 base pairs and preferably 19-25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (miRNAs) are small noncoding polynucleotides, about 22 nucleotides long, that direct destruction or translational repression of their mRNA targets. Antisense polynucleotides comprise sequence that is complimentary to an gene or mRNA. Antisense polynucleotides include, but are not limited to: morpholinos, 2'-O-methyl polynucleotides, DNA, RNA and the like. The polynucleotide-based expression inhibitor may be polymerized in vitro, recombinant, contain chimeric sequences, or derivatives of these groups. The polynucleotide-based expression inhibitor may contain ribonucleotides, deoxyribo-nucleotides, synthetic nucleotides, or any suitable combination such that the target RNA and/or gene is inhibited.

EXAMPLES

Example 1

Drug Delivery to Cells Using Anionic Maleic Anhydride-based Polymers

To assess the ability of these polymers to aid in the delivery of a biologically active compound we chose to assess the ability of these polymers to deliver an antisense oligonucleotide.

Phosphorodiamidate morpholino oligonucleotides (PMOs) are a class of antisense oligomers that have been shown to be extremely effective at inhibiting specific gene expression in vivo [Heasman et al. 2000; Nasevicius et al. 2000]. These antisense agents exert their effects by steric hindrance mechanisms and can be used to block translation or splicing of a target RNA [Kang et al. 1998; Giles et al. 1999; Ghosh et al. 2000]. PMOs are uncharged nucleotide analogs in which a six-membered morpholine ring is substituted for ribose and an uncharged phosphorodiamidate linkage replaces the phosphodiester linkage [Summerton et al. 1997]. Like PEG, charged and uncharged antisense oligomers can be internalized by endocytosis [Carrasco 1994], but are unable to diffuse across cell membranes [Akhtar et al 1991; Akhtar et al. 2000].

To deliver anionic oligos, cationic lipids [Hope et al. 1998; Audouy et al. 2001] and polymers [Robaczewska et al. 2001] that are effective at plasmid DNA delivery are commonly used. However, in order to use these strategies for the delivery of uncharged oligonucleotides such as PMO's, the PMO must first be complexed with a complimentary strand of anionic oligonucleotide to form a charged complex. Two other methods for delivering PMOs, scrape-loading and syringe-loading, both involve physically damaging cells to create transient lesions in the plasma membrane [Ghosh et al. 2000].

To assay the delivery of PMO by hydrophobic polyanions, we used a commercially available HeLa cell line that carries an integrated luciferase gene with a mutant splice site [Kang et al. 1998]. This mutant splice site results in production of an mRNA coding for a truncated inactive luciferase protein. The blocking PMO base pairs to and thus blocks this splice site, thereby enabling expression of the full-length active enzyme. Thus, the level of expression of luciferase in this cell line is directly proportional to the amount of PMO that can be delivered to the nucleus.

Co-incubation of 2.5 µM blocking PMO with various of amphiphilic polyanions including PPA, SMA, BVEMA and their derivatives resulted in increased production of luciferase. The amount of light units, which is proportional to the amount of luciferase produced, is normalized to the cells grown in the absence of delivery agents.

TABLE 1

Cellular delivery of morpholino drug using maleic anhydride-based polymers.

| | Fold increase in Relative Light Units | |
|---|---|---|
| Agent | Opti-DMEM (serum free) | Growth media + 10% serum |
| PPA (20 µg) | 27 | 1 |
| BVEMA (80 µg) | 1 | — |
| P-BVEMA (80 µg) | 3 | 5 |
| P-BVEMA (320 µg) | — | 15 |
| M-BVEMA (80 µg) | 2 | 6 |
| M-BVEMA (320 µg) | — | 8 |
| SMA diacid (500 µg) | | 1 |
| Butyl ester of SMA (500 µg) | | 1.6 |
| propyl amide of SMA | | 1 |

The polyanion PPA is a very good delivery agent in serum-free media as one would expect from published data. However, addition of serum proteins to the growth media completely inhibited any delivery by PPA.

As mentioned previously, the polyanion SMA has been studied as a drug delivery vehicle solely for its ability, as seen for other polymers, to sequester in tumors by the EPR effect. Very little has been published regarding the membrane activity of SMA; however, it has been reported that the cell binding ability of SMA is dependent on the pH and temperature of the media [Oda et al. 1987]. The temperature dependence of cell binding suggests that the increased binding at acidic pH may be not be due to changes in SMA itself, whose protonation should be temperature insensitive, but due to change in the cellular membrane.

It should be noted that the values in the table are for the maximum amount of polyanion that we can add with seeing any toxicity. Attempts to increase delivery by increasing the amount of PPA and butyl ester of SMA resulted in considerable cell death, observed as a decrease in cell confluency.

In contrast to PPA and SMA-based polyanions, delivery assistance by BVEMA-derived polyanions appears to be active in the presence of serum proteins. The most hydrophobic polymer of the BVEMA series is the propyl amide derivative, which gave the highest levels of oligonucleotide delivery in the presence of serum proteins.

These delivery results are important because they demonstrate that the polyanions are able to deliver biologically active compounds. Furthermore, the PMOs were not only delivered to the cytoplasm, their diffusion into the nucleus was unobstructed.

Example 2

Copolymerization of Maleic Anhydride with Alkyl Vinyl Ethers VEMA

Maleic Anhydride (1 mol eq.) and azobisisobutylronitrile (0.01 to 0.1 mole eq) are dissolved in degassed anhydrous toluene in 30 ml screw top vial. To this alkyl vinyl ether (1.5 mol. Eq) is added and the tube is vial is flushed with nitrogen, and placed in a sand bath at 50° C. for 6 to 24 h. After polymerization time is completed the contents of the vial are poured into boiling pet ether (150° C. b.p.) and recovered by filtration, and washed with dry methanol and dried under high vacuum. The alkyl vinyl ethers that may be used are $C_2$-$C_{18}$. In particular, butylvinyl ether may be used.

Example 3

Synthesis of Esters of Copolyvinylether-maleic Anhydride (VEMA)

To a solution of VEMA in anhydrous THF is added 100 eq of alcohol (relative to the anhydride functional group of VEMA). To this solution is added 1 mol % HCl or $H_2SO_4$. The solution is stirred overnight. To this solution is added water and the precipitated polymer is isolated. The polymer is then dissolved in water by bringing the pH to 7.5 by addition of $NaHCO_3$. The polymer is then precipitated out of solution by acidification with HCl to bring the pH to 2. The polymer is then dissolved again in water at pH 7.5 with $NaHCO_3$. A variety of alcohols may be used to synthesize the esters. In particular methyl, ethyl, propyl and butyl alcohols may be used.

Example 4

Synthesis of Amides of Copolyvinylether-maleic Anhydride (VEMA)

To a solution of amine in water is added 1 mol % eq of VEMA (relative to the anhydride functional group of VEMA). The solution is stirred overnight. The polymer is then precipitated out of solution by acidification with HCl to bring the pH to 2. The polymer is then isolated and dissolved again in water at pH 7.5 with $NaHCO_3$. A variety of alcohols may be used to synthesize the esters. In particular methyl, ethyl, propyl and butyl amines may be used.

Example 5

Synthesis of Styrene-Maleic Anhydride (SMA) Copolymer Derivatives

SMA polymer containing 50% styrene and 50% maleic anhydride Mw 1,400 was purchased from Polyscience Inc (Warrington, Pa.).

SMA-diacid; 100 mg SMA polymer was reacted with 100 mg sodium hydroxide in 50 mL of water for 16 h. The aqueous solution was then place in 14,000 MW cutoff dialysis tubing and dialyzed against 80 L water for 72 h. The polymer solution was then removed from the dialysis tubing, and precipitated by addition of HCl to bring to pH to 2. A stock solution of SMA-diacid was then formed by dissolving in water and sodium hydroxide to bring to pH 6.

Butyl ester of SMA, 100 mg SMA polymer was reacted with 0.5 mL of butyl alcohol in 15 mL anhydrous tetrahydrofuran (THF) for 16 h. The THF was removed by rotary evaporation and the polymer was dissolved by water and sodium hydroxide. The aqueous solution was then place in 14,000 MW cutoff dialysis tubing and dialyzed against 80 L water for 72 h. The polymer solution was then removed from the dialysis tubing, and precipitated by addition of HCl to bring to pH to 2. A stock solution of SMA-butyl ester was then formed by dissolving in water and sodium hydroxide to bring the pH to 6.

Propyl amide of SMA; 100 mg SMA polymer was reacted with 0.5 mL of propyl amine in 15 mL methanol for 16 h. The methanol was removed by rotoryevaporation and the polymer was dissolved by water and sodium hydroxide. The aqueous solution was then place in 14,000 MW cutoff dialysis tubing and dialyzed against 80 L water for 72 h. The polymer solution was then removed from the dialysis tubing, and precipitated by addition of HCl to bring to pH to 2. A stock solution of SMA-butyl ester was then formed by dissolving in water and sodium hydroxide to bring the pH to 6.

Example 6

Synthesis of Polypropylacrylic Acid

Propylacrylic acid was synthesized according to Borszeky et al [Borszeky et al. 1997]. Propylacrylic acid was polymerized according to Lackey et al [Lackey et al. 1999]. Propylacrylic acid was mixed with 1 mol % azobisisobutyronitrile and heated to 60° C. for 16 h. Ether was added to the reaction mixture and the polymer precipitate was isolated.

Example 7

Hemolysis Assay

The membrane activity of polymers and peptides was measured using a red blood cell (RBC) hemolysis assay. Porcine whole blood was isolated in heparin-containing vacutainers. The RBC's were isolated by centrifugation at 2,500 RPM for 5 min. They were washed three times with 100 mM dibasic sodium phosphate at the desired pH, and resuspended to the initial volume. The desired pH phosphate buffer was obtained by acidification of a dibasic sodium phosphate stock. Attempts to reach desired acidic pH's with monobasic phosphate resulted in hemolysis. 20 μl of the washed RBC suspension, which is approximately $10^8$ cells [Lackey et al.

1999] was added to 500 µL of phosphate buffer. To this solution was added 20 µg of polymer. The samples were incubated for an hour and a half in a 37 °C. incubator. They were then spun for 1 min at 14,000 RPM. Lysis was determined by measuring the absorbance of the supernatant at 541 nm. Percent hemolysis was calculated assuming 100% lysis to be the absorbance of hemoglobin released upon addition of deionized water, all sample absorbances had the absorbance of buffer alone subtracted.

Example 8

Morpholino Delivery Assay

HeLa Tet-Off cells (Clontech Laboratories, Palo Alto, Calif.) were grown in Delbecco's Modified Eagle's Medium (DMEM, Cellgro, Herndon, Va.) containing 10% fetal bovine serum (FBS) (Hyclone Laboratories, Logan, Utah) in a humidified incubator at 37° C. with 5% CO2 atmosphere. The cells were plated in 24-well culture dishes at a density of 3×106 cells/well and incubated for 24 hours. Medium was replaced with 0.5 ml DMEM, with or without 10% FBS, containing 0.5 µmol morpholino (CCT CTT ACC TCA GTT ACA ATT TAT A, SEQ ID NO: 1, Gene Tools, Philomath, Oreg.) and either containing or not containing 20 µg of various polyanions. The cells were incubated for 4 hours in a humidified, 5% CO2 incubator at 37° C. The media was then replaced with Dubelco's modified Eagle Media containing 10% fetal bovine serum. The cells were then incubated for 48 h. The cells were then harvested and the lysate was then assayed for luciferase expression as previously reported [Wolff et al. 1990]. A Lumat LB 9507 (EG&G Berthold, Bad-Wildbad, Germany) luminometer was used. The amount of luciferase produced in the presence of morpholino and polyanion was normalized to the amount produced in the absence of polyanion and reported in Table 1.

Example 9

Synthesis of Disulfide-containing Butyl Amide of Copolyvinylether-maleic Anhydride (DBVEMA)

To a solution of n-butylamine and cystamine (at a 50 to 1 molar ratio) in water is added 1 mol % eq (anhydride functional group of VEMA relative to amine groups) of VEMA. The solution is stirred overnight. The polymer is then precipitated out of solution by acidification with HCl to bring the pH to 2. The polymer is then isolated and dissolved again in water at pH 7.5 with NaHCO$_3$ in the presence of 10 molar equivalents of dithiothreitol (relative to starting cystamine). After 4 hours, the polymer is then precipitated out of solution by acidification with HCl to bring the pH to 2. The polymer is then isolated and dissolved again in water at pH 7.5 with NaHCO$_3$ in the presence of 10 molar equivalents of 2,2'-dithiodipyridine (relative to starting cystamine). After 4 hours, the polymer is then precipitated out of solution by acidification with HCl to bring the pH to 2. The polymer is then isolated and dissolved again in water. The presence of the thiopyridine is confirmed by measurement of the polymer's absorbance at 280 nm. The thiopyridine may used to conjugate any thiol-containing molecule. A variety of amines may be used to synthesize the amides. In particular methyl, ethyl, propyl and butyl amines may be used.

Example 10

Conjugation of Morpholino Oligonucleotide and Disulfide-containing Butyl Amide of Copolyvinylether-maleic Anhydride (DBVEMA)

Amine-terminal morpholino oligonucleotide was modified with N-Succinimidyl-S-acetylthioacetate (SATA, Pierce Biotechnology Inc) according to manufacturer's protocol. The acetyl group of SATA was removed according to manufacturer's protocol to produce thiol-modified morpholino oligonucleotide, which was conjugated to DBVEMA. 50 pmol was added to 500 µg DBVEMA in 25 µL of 5 mM HEPES pH7.8. The activity of the morpholino oligonucleotide was assayed as before.

| Sample | relative light units |
|---|---|
| morpholino-DBVEMA conjugate | 41710 |
| morpholino alone | 5780 |

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. A process for delivering a polynucleotide to the cytoplasm of a cell in vitro consisting of:
   a) forming a styrene-maleic anhydride random copolymer having 50% styrene and 50% maleic anhydride;
   b) increasing hydrophobicity of the copolymer by reacting the anhydride monomers in the copolymer with hydrophobic amines or hydrophobic alcohols thereby forming a membrane active polyanion capable of lysing mammalian cell membranes at pH 6.5; and
   c) contacting said cell with said polynucleotide and said membrane active polyanion such that the polynucleotide and the membrane active polyanion are endocytosed by the cell.

2. The process of claim 1 wherein increasing hydrophobicity of the copolymer consists of reacting the anhydride monomers in the copolymer with hydrophobic amines.

3. A process for delivering a polynucleotide to the cytoplasm of a cell in vitro consisting of:
   a) forming a butyl vinyl ether-maleic anhydride alternating copolymer;
   b) increasing hydrophobicity of the copolymer by reacting the anhydride monomers in the copolymer with hydrophobic amines or hydrophobic alcohols thereby forming a membrane active polyanion capable of lysing mammalian cell membranes at pH 6.5; and
   c) contacting said cell with said polynucleotide and said membrane active polyanion such that the polynucleotide and the membrane active polyanion are endocytosed by the cell.

4. The process of claim 3 wherein increasing hydrophobicity of the copolymer consists of reacting the anhydride monomers in the copolymer with hydrophobic amines.

* * * * *

SEQUENCE LISTING

<160> NUMBER OF SEQ ID NOS: 1

<210> SEQ ID NO 1
<211> LENGTH: 25
<212> TYPE: DNA
<213> ORGANISM: Artificial
<220> FEATURE:
<223> OTHER INFORMATION: corrects an mRNA splicing error

<400> SEQUENCE: 1
cctcttacct cagttacaat ttata                                    25